United States Patent [19]

Degischer et al.

[11] 4,169,847

[45] Oct. 2, 1979

[54] PROCESS FOR THE MANUFACTURE OF α-CHLOROALKANOYL CHLORIDES

[75] Inventors: Gerhard Degischer, Füllinsdorf; Werner Angst, Muttenz; Mario Valloton, Monthey, all of Switzerland

[73] Assignee: Säurefabrik Schweizerhall, Schweizerhalle, Switzerland

[21] Appl. No.: 812,625

[22] Filed: Jul. 5, 1977

[30] Foreign Application Priority Data

Jul. 7, 1976 [CH] Switzerland .................. 8700/76

[51] Int. Cl.² .......................................... C07C 53/14
[52] U.S. Cl. ...................................... 260/544 Y
[58] Field of Search ............................ 260/544 Y

[56] References Cited

U.S. PATENT DOCUMENTS 3,880,923  4/1975  Scheidmeir et al. ............. 260/544 Y

FOREIGN PATENT DOCUMENTS 1768536  5/1971  Fed. Rep. of Germany ...... 260/544 Y
2263580  7/1974  Fed. Rep. of Germany ...... 260/544 Y

OTHER PUBLICATIONS

Chemical Abstracts, vol. 79, col. 37065(g), (1973).
Chemical Abstracts, vol. 76, col. 139941(v), (1972).

*Primary Examiner*—Gerald A. Schwartz
*Attorney, Agent, or Firm*—Wenderoth, Lind & Ponack

[57] ABSTRACT

An improved process for the production of α-chloroalkanoyl chlorides by reaction of alkanoyl chlorides with chlorine at elevated temperatures is described in which process chlorosulphonic acid is used as catalyst.

8 Claims, No Drawings

PROCESS FOR THE MANUFACTURE OF α-CHLOROALKANOYL CHLORIDES

The invention provides a process for the manufacture of α-chloroalkanoyl chlorides by chlorination of alkanoyl chlorides which contain a substitutable hydrogen atom in the α-position, with chlorine at elevated temperature, using a catalyst.

Conventional processes for the manufacture of α-chloroalkanoyl chlorides, in particular of chloroacetyl chloride, start from the corresponding α-chlorocarboxylic acids. The conversion into the acid chlorides is carried out with reagents, such as phosgene, chlorides of phosphorus or sulphur etc. These reagents must be used in stoichiometric amount, they form by-products during the reaction (CO, phosphoric acids, $SO_2$) which cannot be utilised again, and they are to some extent difficult to work with (e.g. phosgene).

The direct α-chlorination of the corresponding carboxylic acid chlorides therefore presents itself as a more economic process. Normally, however, this direct chlorination proceeds very slowly and unselectively to form polychlorinated products. To avoid these disadvantages, it has been proposed in DOS No. 2,263,580 to carry out the chlorination in the presence of concentrated sulphuric acid as catalyst. However, a crucial drawback occurs in the use of this process when working up the reaction mixture, since the separation of the catalyst proves exceedingly difficult. In the customary separation of the α-chloroalkanoyl chloride by distillation, the concentrated sulphuric acid causes decomposition and condensation reactions, which result in a substantial reduction in the yield of α-chloroalkanoyl chlorides. To keep the formation of by-products within bounds, the distillation must be carried out in vacuo, even in the manufacture of low boiling end products. In addition, a brown resinous residue remains in the apparatus, which is consequently difficult to clean.

It has now been found that the disadvantages referred to above can be avoided by carrying out the chlorination in the presence of chlorosulphonic acid.

The process of the present invention for the manufacture of α-chloroalkanoyl chlorides of the formula

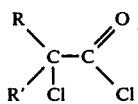
(1)

wherein each of R and R' independently represents a hydrogen atom or an alkyl radical, by reacting alkanoyl chlorides of the formula

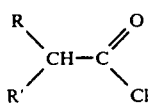
(2)

wherein R and R' are as defined in formula (1), with chlorine at elevated temperature, accordingly comprises carrying out the reaction in the presence of chlorosulphonic acid.

Alkyl radicals R and R' in formula (1) have from 1 to 12 carbon atoms and one radical R or R' is preferably hydrogen.

A preferred process is that for the manufacture of compounds of the formula (1), wherein each of R and R' represents a hydrogen atom or a branched or unbranched alkyl radical of 1 to 6, in particular 1 to 4, carbon atoms, most especially of those compounds in which R represents hydrogen and R' represents an alkyl radical of 1 to 4 carbon atoms.

The manufacture of chloroacetyl chloride is of very particular industrial importance.

The reaction is advantageously carried out at temperatures between 40° and 110° C., preferably between 60° and 85° C.

The chlorosulphonic acid which can be used according to the invention as catalyst is advantageously used in an amount of 0.1 to 10 percent by weight, referred to the alkanoyl chloride employed. Preferably 0.1 to 2, in particular 1 to 2, percent by weight of chlorosulphonic acid is used.

The process can be carried out discontinuously or continuously. All apparatus which can be used for the reaction of fluids with gases is suitable for the reaction.

The reaction is preferably carried out without a solvent by introducing chlorine direct into the liquid acid chloride. The respective acid chloride can also however be dissolved in a suitable inert solvent. The separation of the resultant α-chloroalkanoyl chlorides from unreacted starting material and catalyst is effected preferably by fractional distillation. Non-chlorinated acid chloride can be fed back into the reaction mixture again.

In practice, it proves expedient not to bring the reaction entirely to completion, but to discontinue it at a degree of chlorination of 60 to 99, in particular 75 to 90. The degree of chlorination is defined as follows:

$$\text{degree of chlorination} = \frac{\text{moles of } CAC \times 100}{\text{moles of } AC + \text{moles of } CAC + \text{moles of } DCAC}$$

wherein
CAC=chloroalkanoyl chloride
AC=alkanoyl chloride
DCAC=dichloroalkanoyl chloride and higher chlorination products.

Preferably the process is carried out continuously, with the degree of chlorination referred to above being constantly maintained in the reaction mixture. Such a continuous process is carried out for example as follows: A circulating reactor is charged with the respective acid chloride together with a corresponding amount of chlorosulphonic acid (e.g. 1%) and chlorine is introduced until the content of α-chloroalkanoyl chloride corresponding to the desired degree of chlorination is attained. Alternatively, the reactor can also be charged from the start with acid chloride and α-chloroalkanoyl chloride, in a ratio corresponding to the desired degree of chlorination, together with the corresponding amount of chlorosulphonic acid. Then acid chloride (with chlorosulphonic acid to make up the amount of catalyst) and chlorine are introduced, while simultaneously the mixture containing α-chloroalkanoyl chloride is withdrawn continuously. This mixture is distilled to remove the catalyst. The distillation is carried out for example in a wetted-wall tube, optionally in vacuo. For instance, chloroacetyl chloride obtained as end product is distilled off under normal pressure at temperatures between 110° and 180° C., preferably between 140° and 160° C.

The α-chloroalkanoyl chlorides which can be manufactured according to the invention, in particular chloroacetyl chloride, are used as intermediates for obtaining various plant protection products (cf. for example U.S. Pat. No. 2,863,752).

The following Examples will serve to illustrate the invention. The percentages are by weight.

EXAMPLE 1

A circulating reactor of 500 ml capacity is charged with a mixture of 16% of acetyl chloride, 83% of chloroacetyl chloride and 1% of chlorosulphonic acid. At a temperature of 77° C., 16 liters of chlorine and 50 ml of acetyl chloride, which contains 1% of chlorosulphonic acid, are introduced per hour. The reaction mixture is continuously withdrawn from the top end of the reaction vessel and its composition determined by gas chromatography. (The results are reported in Table 1).

To separate the individual reaction mixture components, 40 ml of a mixture of the composition: 13.6% of acetyl chloride, 84.5% of chloroacetyl chloride, 0.4% of dichloroacetyl chloride, 1% of chlorosulphonic acid and 0.5% of higher boiling components, are measured per minute for example into a wetted-wall tube with approx. 250 cm$^2$ surface area. The column is heated with oil (oil temperature 150° C.). The residue is concentrated again under the same conditions and both distillates are combined. In this way, 98% of the mixture is distilled off. The distillate has the following composition: 99.6% of acetyl chloride+chloroacetyl chloride+dichloroacetyl chloride, 0.4% of condensation products.

Chloroacetyl chloride can be separated from acetyl chloride by fractional distillation. The acetyl chloride thereby obtained can be fed back again into the reaction process.

EXAMPLE 2

The procedure of Example 1 is repeated, using 0.1% of chlorosulphonic acid as catalyst.

EXAMPLE 3

The procedure of Example 1 is repeated, using 0.5% of chlorosulphonic acid as catalyst.

EXAMPLE 4

The procedure of Example 1 is repeated, using 2% of chlorosulphonic acid as catalyst. The analyses by gas chromatography of the separated reaction mixtures of Examples 2 to 4 are also reported in Table 1.

EXAMPLE 5

A circulating reactor (capacity 2 liters), equipped with circulating pump, is charged with 1900 g of a mixture of the same composition as in Example 1. At a temperature of 77° C., 36 liters of chlorine and 150 ml of acetyl chloride, which contains 1% of chlorosulphonic acid, are introduced per hour. The reaction mixture is drawn off at the top end of the reaction vessel. After 14 hours, altogether 2590 g of reaction mixture are obtained. Analysis by gas chromatography shows that this mixture contains 85.8% of chloroacetyl chloride, 13.6% of acetyl chloride and 0.6% of dichloroacetyl chloride. The chlorine conversion is 100%.

The separation of the chloroacetyl chloride from the reaction mixture is effected as described in Example 1.

EXAMPLE 6

The procedure of Example 5 is repeated, but at a temperature of 60° C. After 8 hours, 1686 g of reaction mixture are obtained. Analysis by gas chromatography shows that this mixture contains 82.1% of chloroacetyl chloride, 17% of acetyl chloride and 0.9% of dichloroacetyl chloride. The chlorine conversion is 97%.

EXAMPLE 7

The procedure of Example 5 is repeated, but at a temperature of 70° C. After 13 hours, 2739 g of reaction mixture are obtained. Analysis by gas chromatography shows that this mixture contains 83.8% of chloroacetyl chloride, 15.8% of acetyl chloride and 0.4% of dichloroacetyl chloride. The chlorine conversion is 100%.

EXAMPLE 8

The procedure of Example 5 is repeated, but at a temperature of 83° C. After 8 hours, 1690 g of reaction mixture are obtained. Analysis by gas chromatography shows that this mixture contains 84.1% of chloroacetyl chloride, 15.1% of acetyl chloride and 0.8% of dichloroacetyl chloride.

The term "chlorine conversion" used in Examples 5 to 7 is defined as follows:

chlorine conversion =
$$\frac{(\text{moles of } CAC + 2 \times \text{moles of } DCAC) \times 100}{\text{moles of } Cl_2}$$

CAC = chloroacetyl chloride

TABLE I

| | Composition of the reaction mixture in % (analysis by gas chromatography) | | | | | | | | | | | |
|---|---|---|---|---|---|---|---|---|---|---|---|---|
| | Start | | | | after 2 hrs. | | | | after 4 hrs. | | | |
| Example | AC | CAC | DCAC | HBP | AC | CAC | DCAC | HBP | AC | CAC | DCAC | HBP |
| 1 | 15.7 | 83.2 | 0.24 | 0.81 | 16.9 | 82.4 | 0.26 | 0.37 | 13.5 | 85.6 | 0.52 | 0.35 |
| 2 | 16.0 | 83.2 | 0.40 | 0.06 | 17.3 | 77.9 | 2.84 | 2.01 | 15.7 | 76.7 | 5.39 | 2.25 |
| 3 | 16.4 | 83.0 | 0.43 | 0.17 | 16.0 | 81.0 | 1.57 | 0.82 | 13.7 | 82.4 | 2.38 | 1.57 |
| 4 | 15.4 | 83.3 | 0.44 | 0.87 | 13.3 | 85.8 | 0.47 | 0.39 | 10.9 | 88.2 | 0.56 | 0.34 |
| | | | | | | after 6 hrs. | | | | after 8 hrs. | | |
| | | | | Example | AC | CAC | DCAC | HBP | AC | CAC | DCAC | HBP |
| | | | | 1 | 9.9 | 88.6 | 0.62 | 0.81 | 13.4 | 85.2 | 0.56 | 0.82 |
| | | | | 2 | 15.6 | 72.3 | 6.95 | 4.7 | | | | |
| | | | | 3 | 11.2 | 83.6 | 3.63 | 1.50 | | | | |
| | | | | 4 | 9.0 | 89.6 | 0.74 | 0.86 | 16.4 | 82.2 | 0.48 | 0.86 |

AC :acetyl chloride
CAC :chloroacetyl chloride
DCAC :dichloroacetyl chloride
HBP :products with higher boiling points
The chlorosulphonic acid contained in the reaction mixture was not included in the analysis by gas chromatography.

DCAC=dichloroacetyl chloride

EXAMPLE 9

Chlorine gas (6.3 l/hr) is introduced in the course of 9 hours into a mixture of 250 g of propionyl chloride and 2.5 g of chlorosulphonic acid which has been heated to 80° C. The yield of α-chloropropionyl chloride, which is determined every 2 hours, is 30% after 3 hours, 46% after 5 hours, 55% after 7 hours, and 83% after 9 hours. The separation of the α-chloropropionyl chloride is effected by fractional distillation. The propionyl chloride which is obtained can be used for a further chlorination.

EXAMPLE 10

Chlorine gas (6.3 l/hr) is introduced in the course of 8 hours into a mixture of 250 g of butyryl chloride and 2.5 g of chlorosulphonic acid which has been heated to 80° C. The yield of α-chlorobutyryl chloride is 32% after 6 hours and 50% after 8 hours. The separation of the α-chlorobutyryl chloride is effected by fractional distillation.

What we claim is:

1. A process for the manufacture of α-chloroalkanoyl chlorides of the formula

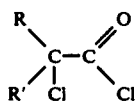 (1)

wherein each of R and R' independently represents a hydrogen atom or an alkyl radical, by reacting alkanoyl chlorides of the formula

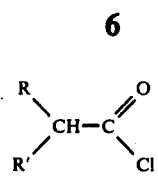 (2)

wherein R and R' are as defined in formula (1) above, with chlorine at elevated temperature of between 40° and 110° C., which process comprises carrying out the reaction in the presence of chlorosulphonic acid as catalyst in an amount of 0.1 to 2 percent by weight.

2. A process according to claim 1 which comprises the use of an alkanoyl chloride of the formula (2), wherein each of R and R' represents hydrogen or an alkyl radical of 1 to 4 carbon atoms.

3. A process according to claim 2 which comprises the use of an alkanoyl chloride of the formula (2), wherein R represents an alkyl radical of 1 to 4 carbon atoms and R' represents hydrogen.

4. A process according to claim 3 for the manufacture of chloroacetyl chloride, wherein acetyl chloride is used as compound of the formula (2).

5. A process according to claim 1, wherein the reaction is carried out at a temperature between 60° and 85° C.

6. A process according to claim 1, wherein the reaction is carried out continuously.

7. A process according to claim 7, wherein a degree of chlorination of 60 to 99 is maintained during the reaction.

8. A process according to claim 1, wherein the α-chloroalkanoyl chloride is separated from the reaction mixture by fractional distillation.

* * * * *